US00PP26730P2

(12) United States Plant Patent
Hurd

(10) Patent No.: US PP26,730 P2
(45) Date of Patent: May 10, 2016

(54) *TIARELLA* PLANT NAMED 'JADE PEACOCK'

(50) Latin Name: ***Tiarella* hybrid**
Varietal Denomination: Jade Peacock

(71) Applicant: Kevin A. Hurd, Austin, TX (US)

(72) Inventor: Kevin A. Hurd, Austin, TX (US)

(73) Assignee: Walters Gardens Inc, Zeeland, MI (US)

( * ) Notice: Subject to any disclaimer, the term of this patent is extended or adjusted under 35 U.S.C. 154(b) by 94 days.

(21) Appl. No.: 14/120,514

(22) Filed: May 28, 2014

(51) Int. Cl.
*A01H 5/02* (2006.01)

(52) U.S. Cl.
USPC ..... Plt./486

(58) Field of Classification Search
USPC ..... Plt./486
See application file for complete search history.

(56) References Cited

U.S. PATENT DOCUMENTS

PP22,258 P2 * 11/2011 Adam ..... Plt./486

* cited by examiner

*Primary Examiner* — June Hwu

(57) ABSTRACT

The new hybrid plant cultivar of *Tiarella* 'Jade Peacock' has moderately lobed glossy foliage of light green with center burgundy palm in the spring. Leaves develop into jade green later in summer and greyed-purple tinting in winter. The mounded, non-running habit is topped by light pink flowers on tightly clustered racemes over a prolonged period beginning in early May.

1 Drawing Sheet

Botanical denomination: *Tiarella* hybrid.
Cultivar designation: 'Jade Peacock'.

BACKGROUND OF THE INVENTION

The present invention relates to a new and distinct cultivar of Foamflower in the Saxifragaceae family and given the cultivar name of 'Jade Peacock'. *Tiarella* 'Jade Peacock' resulted from a cross between *Tiarella* 'Pink Brushes' U.S. Plant Pat. No. 13,329 and *Tiarella* 'Cascade Creeper' U.S. Plant Pat. No. 21,925 and was originally assigned the breeder code K11-14-04. The new plant was hybridized on Mar. 8, 2011, sown on Apr. 4, 2011 and initially selected from among other seedlings growing at a nursery in Zeeland, Mich. in the summer of 2011 by the inventor Kevin A. Hurd. *Tiarella* 'Jade Peacock' has been asexually propagated by division and by careful tissue culture propagation at the same nursery in Zeeland, Mich., and the resultant asexual propagules have been remained stable and exhibit the same characteristics as the original plant in multiple generations.

BRIEF SUMMARY OF THE INVENTION

The nearest comparison varieties known to the applicant are the parents, *Tiarella* 'Pink Brushes' U.S. Plant Pat. No. 13,329 and *Tiarella* 'Cascade Creeper' U.S. Plant Pat. No. 21,925 along with *Tiarella* 'Sugar and Spice' U.S. Plant Pat. No. 16,738 and *Tiarella* 'Spring Symphony' U.S. Plant Pat. No. 12,397.

Compared to *Tiarella* 'Jade Peacock', 'Pink Brushes' has thinner and less pronounced center purple palm throughout the year and the racemes are less dense and numerous. 'Cascade Creeper' has foliage that is more deeply lobed and the racemes are more spread out and less numerous, and the flower buds are more pink. 'Sugar and Spice' has more acute leaf apices and flower racemes less tightly arranged than *Tiarella* 'Jade Peacock' and 'Iron Butterfly' has less numerous racemes of light pink flowers with fewer flowers per raceme and is effective for a shorter period of time.

*Tiarella* 'Jade Peacock' is distinct from all other Foamflower plants known to the applicant in the following combined traits:

1. Light pink flowers densely displayed on numerous singly-branched racemes.
2. Mounded habit with numerous, tall, tightly-packed racemes over a prolonged period.
3. Moderately lobed palmate foliage with glossy surfaces.
4. Foliage color with center burgundy palm surrounded by light green to jade green becoming tinted with greyed-purple in winter.

Additional comparisons of plants with U.S. Plant Patents are presented in Table 1.

TABLE 1

| CULTIVAR | LEAF SURFACE | FLOWER COLOR | SCAPE HEIGHT | LOBES | HABIT |
|---|---|---|---|---|---|
| Tiarella 'Jade Peacock' | glossy | light pink | 43 cm | deep | mounding |
| Tiarella 'Sunset Ridge' U.S. PLANT PAT. NO. 23,628 | glossy | white | 21 cm | shallow | trailing |
| Tiarella 'Pacific Crest' U.S. PLANT PAT. NO. 23,591 | glossy | white | 18 cm | deep | trailing |
| Tiarella 'Oregon Trail' U.S. PLANT PAT NO. 22,712 | matte | white | 31 cm | deep | trailing |
| Tiarella 'Appalachian Trail' U.S. PLANT PAT. NO. 22,675 | matte | white | 31 cm | shallow | trailing |

TABLE 1-continued

| CULTIVAR | LEAF SURFACE | FLOWER COLOR | SCAPE HEIGHT | LOBES | HABIT |
|---|---|---|---|---|---|
| Tiarella 'Stephanie Cohen' U.S. PLANT PAT. NO. 22,258 | glossy | white | 20 cm | deep | mounding |
| Tiarella 'Lehigh' U.S. PLANT PAT. NO. 22,031 | matte | white | 15 cm | medium | running |
| Tiarella 'Delaware' U.S. PLANT PAT. NO. 21,980 | matte | white | 30 cm | shallow | trailing |
| Tiarella 'Wissahickon' U.S. PLANT PAT. NO. 21,963 | matte | white | 30 cm | medium | mounding |
| Tiarella 'Susquehanna' U.S. PLANT PAT. NO. 21,961 | matte | white | 30 cm | medium | running |
| Tiarella 'Happy Trails' U.S. PLANT PAT. NO. 21,933 | glossy | white | 23 cm | medium | running |
| Tiarella 'Cascade Creeper' U.S. PLANT PAT. NO. 21,925 | matte | white | 43 cm | deep | running |
| Tiarella 'Mystic Mist' U.S. PLANT PAT. NO. 21,282 | matte | white | 23 cm | shallow | mounding |
| Tiarella 'Morning Star' U.S. PLANT PAT. NO. 17,486 | glossy | pink | 25 cm | very deep | mounding |
| Tiarella 'Sugar and Spice' U.S. PLANT PAT. NO. 16,738 | glossy | pink | 30 cm | deep | mounding |
| Tiarella 'TNTIA041' U.S. PLANT PAT. NO. 16,734 | matte | near white | 30 cm | very deep | mounding |
| Tiarella 'Candy Striper' U.S. PLANT PAT. NO. 15,528 | matte | white | 30 cm | very deep | mounding |
| Tiarella 'Running Tiger' U.S. PLANT PAT. NO. 15,360 | matte | white | as cm | medium | semi-running |
| Tiarella 'Pirate's Patch' U.S. PLANT PAT. NO. 14,907 | matte | white | 32 cm | shallow | semi-running |
| Tiarella 'Springwood' U.S. PLANT PAT. NO. 14,087 | matte | white | 30 cm | medium | mounding |
| Tiarella 'Seafoam' U.S. PLANT PAT. NO. 13,696 | matte | white | 35 cm | deep | mounding |
| Tiarella 'Black Snowflake' U.S. PLANT PAT. NO. 13,684 | matte | white | 45 cm | shallow | mounding |
| Tiarella 'Pink Pearls' U.S. PLANT PAT NO. 13,445 | matte | white | 40 cm | shallow | mounding |
| Tiarella 'Jeepers Creepers' U.S. PLANT PAT. NO. 13,437 | matte | white | 30 cm | deep | semi-running |

TABLE 1-continued

| CULTIVAR | LEAF SURFACE | FLOWER COLOR | SCAPE HEIGHT | LOBES | HABIT |
|---|---|---|---|---|---|
| Tiarella 'Pink Skyrocket' U.S. PLANT PAT. NO. 13,382 | matte | pink | 28 cm | very deep | mounding |
| Tiarella 'Pink Brushes' U.S. PLANT PAT. NO. 13,329 | matte | pink | 45 cm | medium | mounding |
| Tiarella 'Neon Lights' U.S. PLANT PAT. NO. 13,289 | glossy | light pink | 40 cm | medium | mounding |
| Tiarella 'Starfish' U.S. PLANT PAT. NO. 13,148 | matte | light pink | 32 cm | very deep | mounding |
| Tiarella 'Spring Symphony' U.S. PLANT PAT. NO. 12,397 | matte | light pink | 25 cm | very deep | mounding |
| Tiarella 'Iron Butterfly' U.S. PLANT PAT. NO. 12,396 | glossy | light pink | 22 cm | deep | mounding |
| Tiarella 'Black Velvet' U.S. PLANT PAT. NO. 12,348 | matte | light pink | 35 cm | deep | mounding |
| Tiarella 'Crow Feather' U.S. PLANT PAT. NO. 12,335 | glossy | pink | 30 cm | deep | mounding |
| Tiarella 'Mint Chocolate' U.S. PLANT PAT. NO. 11,379 | matte | pink | 38 cm | medium | mounding |
| Tiarella 'Spanish Cross' U.S. PLANT PAT. NO. 11,345 | glossy | pink | 28 cm | deep | mounding |
| Tiarella 'Ninja' U.S. PLANT PAT. NO. 11,168 | matte | white | 38 cm | deep | mounding |
| Tiarella 'Cygnet' U.S. PLANT PAT. NO. 11051 | matte | pink | 45 cm | very deep | mounding |

BRIEF DESCRIPTION OF THE DRAWINGS

The photographs of *Tiarella* 'Jade Peacock' demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
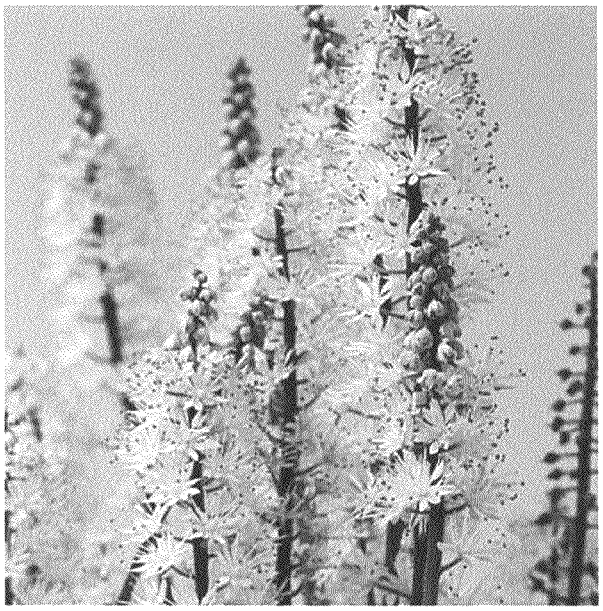
FIG. 1 shows a close-up of the flowers and buds of the new plant in early spring.
Figure 2:
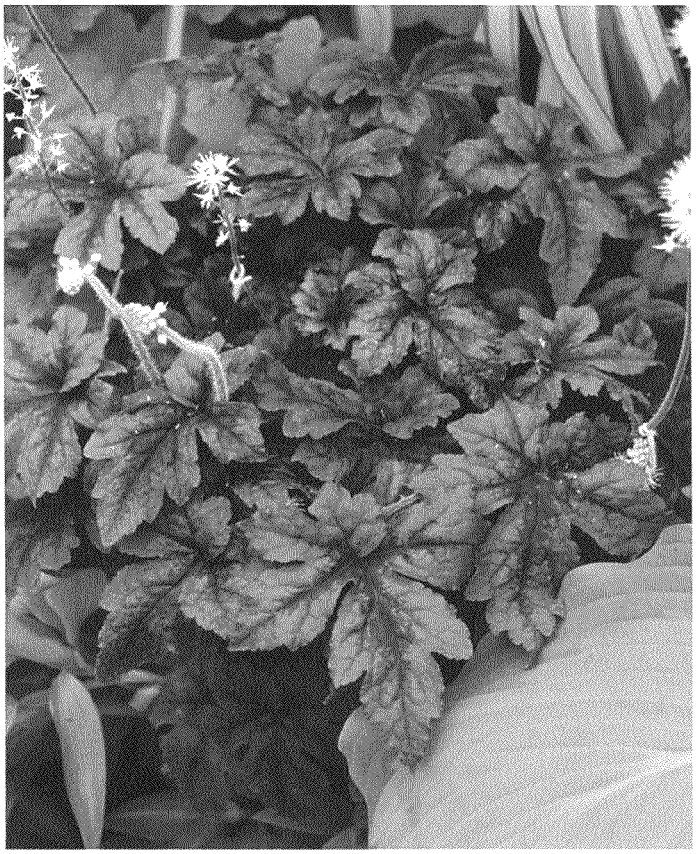
FIG. 2 shows a close-up of the foliage of the new plant in mid-summer with various stages of foliage colors.

The following description is based on a one-year old plant of *Tiarella* 'Jade Peacock' growing in a full sun trial garden with supplemental water and fertilizer in Zeeland, Mich., USA. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage: Female (seed parent) *Tiarella* 'Pink Brushes' U.S. Plant Pat. No. 13,329; male (pollen) *Tiarella* 'Cascade Creeper' U.S. Plant Pat. No. 21,925.

Plant habit: Hardy herbaceous perennial with compact basal shoots each with a basal rosette of foliage; mounded foliage about 18 cm tall and 34 cm in diameter.

Roots: Fibrous, finely branched; color light beige to near white depending on soil type.

Growth rate: Rapid, rooting from cutting in 2 weeks and finishing in three-liter container in about 3 months.

Foliage: Cordate, serrate, palmately five-lobed; pubescent above and below; slightly lustrous above and below.

Leaf blade: To about 13.5 cm long and 12.0 cm wide, average about 9.5 cm long and 8.5 cm across; undulate to lightly concaved downward.

Leaf blade color: Seasonably variable; spring young emerging leaves top and bottom surface nearest RHS 177C with tinting of green and the center marking between RHS 187C and RHS 187B along major veins and spreading out to about 1.0 cm; late spring and summer between RHS 144A and RHS 146C with center palm following main veins between RHS 187C and RHS 187B above and between RHS 146C and RHS 146D underneath without darker center palms; summer and fall mature leaves in full sun nearest RHS 137A with tinting or blush of greyed purple nearest RHS N186A with a dark palm of nearest RHS N186A above, below between RHS 147B and RHS 147C with slight greyed-purple tinting from the upper surface; overwintered leaves top surface nearest RHS 187A in some regions and between RHS 183B and RHS 183C in other regions, with a palm running along major veins nearest RHS N186A, below nearest RHS 182C with darker greyed-purple pigment showing through from above.

Leaf margin: Serrate and hirsutulous.

Leaf apex: Acute.

Leaf base: Cordate with overlapping lobes.

Leaf surface: Hirsutulous both above and below.

Leaf quantity: About 50 per plant.

Veins: Hirsutulous, palmate, slightly impressed above and raised below; same color as surrounding leaf tissue on top and bottom surfaces.

Petiole: Round in cross section, hirsute, about 18.0 cm long and 2.5 mm diameter.

Petiole color: Seasonally variable; overwintered petioles between RHS 176 B and RHS 182A; more red than RHS 177B and more brown than RHS 182A on older foliage; and 145A on emerging foliage.

Inflorescence: In tight, frequently singly-branched raceme; about 45 to 50 racemes per plant in various stages at one time; about 80 flowers per main stem and 20 per branch; about 2.5 cm across; individual racemes flowering starting in early May for about 4 weeks.

Fragrance: Sweetly fragrance.

Peduncle: Round in cross section, hirsute, about 38 cm tall and 2.5 mm in diameter.

Peduncle color: Young developing racemes nearest RHS 162C with green undertones nearest RHS 145C; older nearest RHS 177A with green undertones nearest RHS 138A; upper regions nearest RHS 185A.

Pedicel: Round in cross section, hirsutulous, about 8.0 mm long and 0.5 mm diameter.

Pedicel color: Nearest RHS 185B at base and lighter than RHS 186D at distal end.

Buds: One day prior to opening—oblong, about 3.5 mm long and 2.5 mm diameter.

Bud color: Closest to RHS 73D.

Flower: Perfect, actinomophic, peta1oid sepals, rotate with stamens exserted, about 6.0 mm long and 7.0 mm in diameter at face; individual flowers lasting about 4 days on plant or on cut panicle; flowers dense and outward to slightly upwardly facing.

Petals: Five; spatulate; margin entire, apex narrowly acute, base attenuate; about 3 mm long and 1.0 mm wide; color nearest RHS N155C on both surfaces.

Calyx: Five, oblong-ovate; campanulate, acute apex, about 3.5 mm long and 1.0 mm across; fused in the bottom 1 mm; color nearest RHS 69D.

Androecium: Typically ten.

*Filaments*.—Thin, exserted, about 10 mm long and less than 0.5 mm diameter; color white lighter than RHS 155D.

*Anthers*.—Elliptic; longitudinal, basifixed; about 0.8 mm long and 0.5 mm diameter; color nearest RHS 170B.

*Pollen*.—Abundant; color nearest RHS 170A.

Gynoecium: Carpels two, unequal.

*Style*.—Two, separate; 0.5 and 5.0 mm long and about 1.0 across; lighter than RHS 155D.

*Stigma*.—Miniscule; same color as style.

*Ovary*.—Oblong with pointed apex; about 2.0 mm long and 1.0 mm diameter; color nearest RHS 1D.

Fruit: Two-valved capsule, about 6 mm long and 3 mm in diameter at widest portion; color nearest RHS 199A.

Seed: Ovoid, less than 0.3 mm long and wide; color nearest RHS 200A.

Disease and pest tolerance: The new plant grows best with ample moisture and drainage in some shade. As with most Foamflower plants, 'Jade Peacock', is usually avoided by browsing deer. Cold hardy from USDA zones 4 to 9. Other resistance and tolerance outside of that normal for *Tiarella* is not known.

I claim:

1. The new and distinct Foamflower plant named *Tiarella* 'Jade Peacock' as herein described and illustrated with young spring foliage of light green, maturing to multi-shaded jade green with center burgundy palm and becoming tinted with greyed-purple, having numerous racemes of light pink flowers on tightly congested mounds.

* * * * *